United States Patent [19]

Halloran et al.

[11] Patent Number: 5,180,580
[45] Date of Patent: Jan. 19, 1993

[54] HAIRSTYLING PREPARATIONS CONTAINING AMIDOFUNCTIONAL SILOXANES

[75] Inventors: Daniel J. Halloran; Christine M. Handt, both of Midland, Mich.

[73] Assignee: Dow Corning Corporation, Midland, Mich.

[21] Appl. No.: 833,262

[22] Filed: Feb. 10, 1992

[51] Int. Cl.$^5$ .......................... A61K 7/11; A61K 7/06
[52] U.S. Cl. ....................................... 424/71; 424/70; 424/47; 514/579
[58] Field of Search ............................ 424/47, 70, 71

[56] References Cited

U.S. PATENT DOCUMENTS 4,487,883  12/1984  Homan ............................. 525/370
4,586,518   5/1986  Cornwall .......................... 424/70

Primary Examiner—Thurman K. Page
Assistant Examiner—Sally Gardner
Attorney, Agent, or Firm—Jim L. DeCesare

[57] ABSTRACT

A hairstyling preparation containing at least one anionic or nonionic organic polymeric film forming agent and a solvent. The improvement resides in incorporating into the hairstyling preparation as an ingredient thereof an amidofunctional polysiloxane having an average of fifty to one thousand siloxane units per molecule with an average of one to fifty of the siloxane units per molecule being amide-containing siloxane units.

6 Claims, No Drawings

HAIRSTYLING PREPARATIONS CONTAINING AMIDOFUNCTIONAL SILOXANES

BACKGROUND OF THE INVENTION

This invention relates to a hairstyling preparation which includes the combination of an amidofunctional siloxane polymer and a nonionic or anionic film forming organic polymer resin.

Hairstyling preparations stabilize a hairstyle during or following its creation with a comb, brush or rollers. Hairstyling products in addition should make the hair easier to manage by improving its wet combing or brushing qualities. hairstyling products include setting lotions and hair sprays. Such preparations remain in the hair and are not rinsed out. The main active ingredient in hairstyling products is a polymer resin dissolved in a solvent as a film forming agent which is deposited on the hair after evaporation of the solvent. These preparations also protect the hair to some degree against the action of moisture.

Setting lotions make a hairstyle more durable. They prevent hair from "flying away", reduce the amount of charge when the hair is combed or brushed, improve wet and dry combing, and improve the feel and luster of the hair. A setting lotion should not separate from the hair or form flakes, become tacky or sticky at high humidity, or cause lathering during wet combing of the hair. Setting lotions are normally applied to the hair after it has been washed and towel dried, after which the hair is wound on rollers and dried. Some setting lotions allow the hair to be brushed, combed and dried with a hair dryer following application of the setting lotion to the hair.

Setting lotions contain a polymeric film forming resin and a solvent, and often include compatibility improvers, plasticizers, fragrances, coloring agents, and preservatives. Examples of nonionic polymeric film forming resins are polyvinylpyrrolidone and copolymers of vinylpyrrolidone-vinyl acetate. Examples of anionic film forming resins are copolymers of methyl vinyl ether and maleic acid anhydride; terpolymers of vinyl acetate, crotonic acid and vinyl esters; and graft polymers of vinyl acetate, crotonic acid and polyethylene oxide. Typically, the solvent is either ethanol or isopropanol. Setting lotions are marketed as thin, aqueous-alcoholic solutions; gels; aerosol sprays including propellant and pump sprays; and a mousse which is an aerosol foam.

Hair sprays are used to stabilize the hairstyle against the action of wind and humidity. The hair should appear natural and should not be sticky at high humidity. The hair spray must dry rapidly and should be capable of being removed easily by brushing or combing. Removal of the hair spray must not generate visible dust, and the film which forms on the hair must be clear, colorless, and invisible even on dark hair. Following application of the hair spray, the hair must have a pleasant smell, be glossy and not feel dull.

Aerosol hair sprays are two phase systems which include a liquid phase and a gas phase. The contents of the liquid phase or concentrate are the polymeric film forming resin and the solvent, and in addition plasticizers, lustering agents, and fragrances. The gas phase includes a propellant such as propane, butane, isobutane, pentane and dimethyl ether. Some hair sprays are available as nonaerosol sprays or pump sprays in which the propellant is replaced with additional solvent.

In accordance with the present invention, what has been provided is a hairstyling preparation which contains a novel combination of silicone and polymeric film forming resin. It has been discovered that the silicone ingredient when combined with the polymeric film forming resin imparts improved conditioning benefits to hairstyling preparations.

SUMMARY OF THE INVENTION

The invention is directed to hairstyling compositions and methods of styling hair in which the improvement resides in the inclusion in the hairstyling composition of an amidofunctional polysiloxane.

It is an object of the present invention to provide a hairstyling composition containing an amidofunctional polysiloxane which imparts improved tactile properties to the styled hair.

It is an another object of the present invention to provide a hairstyling composition containing an amidofunctional polysiloxane which imparts to the styled hair good wet combing and a heavy conditioning feel to the styled hair.

It is a further object of the present invention to Provide a hairstyling composition containing an amidofunctional polysiloxane which imparts improved conditioning benefits to the styled hair without detracting from the curl retention characteristics of the hairstyling composition.

These and other objects, features and advantages of the invention will become apparent from a consideration of the following detailed description thereof.

DETAILED DESCRIPTION OF THE INVENTION

The hairstyling preparation in accordance with the present invention includes as ingredients thereof at least one anionic or nonionic organic polymeric film forming resin and a solvent. The improvement resides in the incorporation into the hairstyling preparation as an ingredient thereof, an amidofunctional polysiloxane.

While the organic polymeric film forming resin may constitute any one or more of the numerous conventional anionic and nonionic film forming agents known in the hairstyling art, for purposes of the present invention it is preferably an anionic organic polymeric film forming resin which is a polyacrylate. Most preferably, the film forming agent is a poly(methylvinyl ether/maleic acid) monoethyl ester. These particular film forming agents are available as solutions containing fifty percent solids in ethanol from GAF Chemicals Corporation, Wayne, N.J. USA under the trademarks GANTREZ ® ES-225 and GANTREZ ® SP-215.

Other preferred film forming resins which may be employed in accordance with the present invention are GANTREZ ® ES-425 which is a poly(methylvinyl ether/maleic acid) monobutyl ester, and GANTREZ ® AN-149 which is poly(methylvinyl ether/maleic) anhydride both of which are available from GAF Chemicals Corporation, Wayne, N.J. USA; Stephanhold R-1 and Stephanhold Extra which are polyvinylpyrrolidone/ethyl methacrylate/methacrylic acid terpolymers available from Stephan Company, Northfield, Ill.; and carboxylated polyvinylacetate copolymers which are sold under the trademarks RESYN ® 28-1310 and RESYN ® 28-2930 by the National Starch & Chemical Company, Bridgewater, N.J.

The amidofunctional polysiloxanes which are employed in accordance with the present invention and methods of preparing these organosilicon compounds are known in the art, and the amidofunctional polysiloxanes used herein are commercially available. The amidofunctional polysiloxane and the film forming resin are present in the hairstyling preparation in a weight ratio ranging from 2:1 to 1:2 but preferably the ratio is 1:1.

The amidofunctional polysiloxane is a triorganosiloxane-endblocked polydiorganosiloxane having an average of 50 to 1000 siloxane units per molecule with an average of 1 to 50 of the siloxane units per molecule being amide-containing siloxane units. The amide-containing siloxane units bear a substituent of the formula

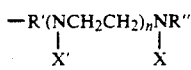

wherein n is 0 or 1, R' denotes an alkylene radical of 3 to 6 carbon atoms, and R" denotes a hydrogen radical or an alkyl radical of 1 to 6 carbon atoms, X denotes an acyl radical of the formula

X' denotes a hydrogen radical or X' and R''' denotes an alkyl radical of 1 to 4 carbon atoms and substantially all other organic substituents in the polydiorganosiloxane being methyl groups.

The amidofunctional silicone component in accordance with this invention consists essentially of a triorganosiloxane-endblocked polydiorganosiloxane which contains amidoalkyl substituents. Triorganosiloxane-endblocked polydiorganosiloxanes (amidofunctional silicone) consist essentially of terminal triorganosiloxane units of the formula $R_3SiO_{\frac{1}{2}}$ and backbone diorganosiloxane units of the formula $R_2SiO_{2/2}$. Trace amounts of other siloxane units in amidofunctional silicone, such as $SiO_{4/2}$ and $RSiO_{3/2}$, which are normally present as impurities in commercial polydiorganosiloxanes may be present. Preferably there are no $SiO_{4/2}$ units or $RSiO_{3/2}$ units in the amidofunctional silicones.

The R radicals of the above siloxane units are substantially either amide-containing radicals of the formula

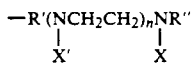

or methyl radicals. Minor amounts of other organic substituents which are normally present as impurities in commercial polydiorganosiloxanes may be present. It should be understood, for example, that the amidofunctional silicones of this invention are often prepared by acylation of corresponding aminofunctional silicones. Consequently, the amidofunctional silicones may also contain residual aminofunctional siloxane units. For example, siloxane units such as $H_2NCH_2CH_2NHCH_2CH(CH_3)CH_2SiO_{2/2}$ or $H_2NCH_2CH_2Ch_2SiO_{2/2/}$ may also be present in the amidofunctional silicones useful in this invention. Nowever, for the purposes of this invention it is preferred to employ silicone oils that do not contain significant levels (more than 25 percent of the number of amidofunctional substituents) of the unmodified aminofunctional siloxane units.

In the formula for the amide-containing radicals, R' denotes an alkylene radical of 3 to 6 carbon atoms, such as —CH₂CH₂CH₂—, —CH₂CH₂CH₂Ch₂—, —CH₂CH(CH₃)CH₂—, —CH₂CH₂CH₂CH₂CH₂—, and —CH₂CH(CH₂CH₃)CH₂—. Anidofunctional silicones wherein the silicon bonded, amide-containing radicals have a trimethylene radical or an alkylated trimethylene radical, such as —CH₂CH(CH₃)CH₂—, as the R' radical are preferred because of ease of synthesis and availability.

R" denotes a hydrogen radical, which is a preferred R" radical, or an alkyl radical of 1 to 6 carbon atoms, such as methyl, ethyl, propyl, butyl, and isobutyl.

In the formula for the amide-containing radicals, n has a value of 0 or 1, so that the radical may contain one or two nitrogen atoms. X denotes an acyl radical of the formula

and X' denotes a hydrogen radical or X. In the acyl radical, R''' denotes an alkyl radical of 1 to 4 carbon atoms such as methyl, ethyl, propyl, isopropyl, or butyl.

In accordance with the above, triorganosiloxane-endblocked polydiorganosiloxanes preferred for use in the method of this invention consists essentially of siloxane units selected from the following:

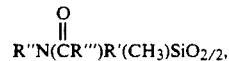

$(CH_3)_3SiO_{1/2}$, and $(CH_3)_2SiO_{2/2}$ where R', R", and R''' have the same meanings as described above. It should be understood that any of the siloxane units having non-acylated nitrogen atoms can also be present in their salt form. It is well known that the salt form occurs when such polymers are neutralized by acids such as mineral acids or carboxylic acids.

The silicone polymers of this invention may contain amide-containing siloxane units of the formula

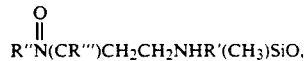

wherein R', R", and R'" have the same meanings as described above. These amide-containing units have a ratio of acyl groups to nitrogen atoms of about 0.5.

For the purpose of illustrating the use of amidofunctional polysiloxanes as hairstyling additives in accordance with the present invention, several hair fixative formulations were prepared using the GANTREZ® ES-225 polymer resin. The formulations contained one gram of an amidofunctional polysiloxane, nine grams of ethanol, and ten grams of ethanol containing ten percent by weight solids of the GANTREZ® AN-149 polymer. In ethanol, GANTREZ® AN-149 which is the polycarboxylic resin formed from vinyl methyl ether and maleic anhydride, reacts to provide its ethyl half-ester GANTREZ® ES-225 which is a polymer consisting of the partial ethyl ester of the polycarboxylic resin formed from vinyl methyl ether and maleic anhydride. The formulas for each of these resin polymers is set as follows:

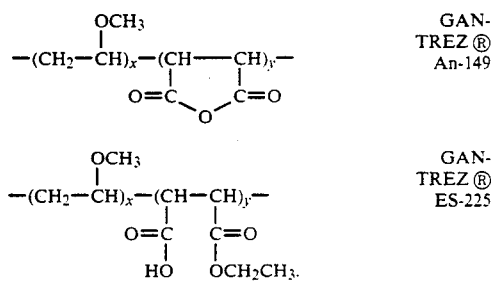

The formulations were each ten percent neutralized with 2-amino-2-methyl-1-propanol. Each formulation was evaluated on hair tresses which were evaluated to contain on an add-on level basis about 0.2 grams of treatment per tress. Each formulation was applied to the hair tress and worked into the hair. The tress was curled with a curling iron for one minute and hung from one end. The length of the curled tress was monitored as a function of time and humidity. Tactile properties of the treated tresses both wet and dry were noted during the procedure. None of the amidofunctional polysiloxanes tested were found to detract from the curl retention or the holding properties of the GANTREZ resin.

The amidofunctional polysiloxanes which were employed had the formula:

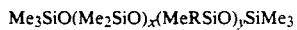

in which Me is methyl; x was 45-500; y was 1-20; and R was

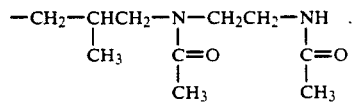

Five amidofunctional polysiloxanes conforming to the above formula were tested including (i) an amidofunctional polysiloxane having a degree of polymerization of fifty and containing two mole percent amide units; (ii) an amidofunctional polysiloxane having a degree of polymerization of fifty and containing 4.5 mole percent amide units; (iii) an amidofunctional polysiloxane having a degree of polymerization of one hundred and containing two mole percent amide units; (iv) an amidofunctional polysiloxane having a degree of polymerization of two hundred and containing 2.5 mole Percent amide units; and (v) an amidofunctional polysiloxane having a degree of polymerization of four hundred and containing 0.5 mole percent amide units. Degree of polymerization is the length of the polymer chain indicated in terms of the number of repeating units in the chain.

Subjective evaluations of the treated hair tresses when compared to a control solution which was free of any amidofunctional polysiloxane indicated that hairstyling preparations containing amidofunctional polysiloxane (i) exhibited improvement in wet combining. Amidofunctional polysiloxanes (iii) and (iv) exhibited improvements in wet feel to the extent that very heavy conditioning effects were apparent. Amidofunctional polysiloxanes (i), (ii) and (v) exhibited improvements in wet feel to the extent that heavy conditioning effects were apparent. Improvement in dry feel was noted for amidofunctional polysiloxanes (i), (iii) and (iv). It was found that the amidofunctional polysiloxanes of the present invention were ethanol compatible and were capable of being added directly to existing hairstyling preparations. Thus, while being generally useful as hairstyling additives, the amidofunctional polysiloxanes of the present invention are particularly suitable for use as conditioning additives in ethanol based hair spray formulations.

This is in contrast to the attempted use of other silicon materials in combination with anionic resins in alcoholic fixatives. Most siloxane materials are insoluble in the alcoholic solvent and are therefore unsuitable. Silicone polyethers are soluble and are used as resin plasticizers, but they do not function as conditioners without sacrificing hair-holding properties. Amino-silicones are well known for their conditioning benefits on hair, but these materials are incompatible with carboxylic acid-functional resins and precipitates are formed. Amido-silicones are soluble in alcoholic fixatives, and they form heterogeneous films with anionic resins, while maintaining solubility and compatibility in solution. They therefore do not function as resin plasticizers and do not detract from resin-delivered hold, but they do function as conditioners, thereby giving rise to a new product form characterized as a conditioning alcoholic fixative.

The hair fixative compositions of this invention may contain an emulsifying agent selected from the group consisting of anionic, amphoteric nonionic, cationic, and zwitterionic surfactants. Suitable anionic detergents include sulfonated and sulfated alkyl, aralkyl and alkaryl anionic detergents; alkyl succinates; alkyl sulfosuccinates and N-alkyl sarcosinates. Surfactants generally classified as amphoteric or ampholytic detergents include, among others, cocoamphocarboxyglycinate, cocoamphocarboxypropionate, cocobetaine, N-cocamidopropyldimethylglycine, and N-lauryl-N-carboxymethyl-N-(2-hydroxyethyl)ethylenediamine.

Other suitable amphoteric detergents include the quaternary cycloimidates, betaines, and sultaines disclosed in U.S. Pat. No. 3,964,500. The compositions of this invention may contain a nonionic surfactant. The nonionic surfactants of the Present invention are selected from the group consisting of fatty acid alkanolamide and amiue oxide surfactants. Appropriate cationic surfactants in accordance with the present invention include quaternary ammonium salts of primary, secondary, and tertiary fatty amines. Zwitterionic surfactants which may be employed are quaternary ammonium, phosphonium, and sulfonium compounds containing aliphatic substituents one of which is carboxy, phosphate, phosphonate, sulfate, or sulfonate functional.

Other adjuvants may be added to the compositions of this invention such as plasticizers, thickeners, perfumes, colorants, electrolytes, pH control ingredients, antimicrobials, antioxidants, ultraviolet light absorbers and medicaments. When the fixative is in the form of a 8el or lotion, it is sometimes preferred to employ a thickener in the compositions to facilitate the hand application of the composition to the hair. Thickeners are preferably used in sufficient quantities to provide a convenient viscosity. For example, viscosities within the range of 400 to 6000 cps are preferred for lotions. Higher viscosities are preferred for gels whereas lower viscosities are preferred for sprays.

Suitable thickeners, include, among others, sodium alginate, gum arabic, polyoxyethylene, guar gum, hydroxypropyl guar gum, cellulose derivatives such as methylcellulose, methylhydroxypropylcellulose. hydroxypropylcellulose, polypropylhydroxyethylcellulose, starch and starch derivatives such as hydroxyethylamylose, and starch amylose, locust bean gum, electrolytes such as NaCl, saccharides such as fructose and glucose, and derivatives of saccharides such as PEG-120 methyl glucose dioleate. Preferred thickeners include the cellulose derivatives and saccharide derivatives. The glucose derivative, PEG-120 methyl glucose dioleate, is especially preferred in the present invention. Electrolytes including sodium chloride and ammonium chloride provide thickening particularly in aqueous systems and may also be employed in accordance with the present invention.

Representative plasticizers that may be employed include polypropylene glycol, glycerine, and polysiloxanes. Siloxane polymers such as polydimethylsiloxane, cyclic polydimethylsiloxane, phenylpolydimethylsiloxane, and polydimethylsiloxane with methylene and/or propylene oxide side chains, are particularly preferred in accordance with the present invention.

The perfumes which can be used in the compositions must be cosmetically acceptable perfumes. Colorants are used to confer a color to the composition and may generally be used. Although not required, it is sometimes Preferred to employ an acid or base to adjust the pH within the range of 5 to 9 or more preferably within the range of 6 to 8 in the compositions of this invention. Any water soluble acid such as a carboxylic acid or a mineral acid is suitable. For example, suitable acids include mineral acids such as hydrochloric, sulfuric, and phosphoric, monocarboxylic acids such as acetic acid, lactic acid, or propionic acid; and polycarboxylic acids such as succinic acid, adipic acid and citric acid. Where a base is required, organic amines such as 2-amino-2-methyl-l-propanol are appropriate.

If for special purposes additional conditioners are desired, they may be added. For example, any of the well-known organic cationic hair conditioning components may be added. Some cationic conditioning components that may be used in the present invention to provide hair grooming include quaternary nitrogen derivatives of cellulose ethers, homopolymers of dimethyldiallyl-ammonium chloride, copolymers of acrylamide and dimethyldiallylammonium chloride, homopolymers or copolymers derived from acrylic acid or methacrylic acid containing cationic nitrogen functional groups attached to the polymer via ester or amide linkages, polycondensation products of N,N'-bis-(2,3-epoxypropyl)-piperazine or of piperazine-bis-acrylamide and piperazine, poly-(dimethylbutenylammonium chloride)-$\alpha,\omega$-bis-(triethanol-ammonium) chloride, and copolymers of vinylpyrrolidone and acrylic acid esters with quaternary nitrogen functionality. The above cationic organic polymers and others are described in more detail in U.S. Patent No. 4,240,450 which is hereby incorporated by reference to further describe the cationic organic polymers. Other categories of organic conditioners may also be employed such as proteins, monomeric organic quaternaries and betaines.

A preservative may be required and representative peservatives which may be employed include about 0.1-0.2 weight percent of compounds such as formaldehyde, dimethyloldimethylhydantoin, 5-bromo-5-nitro-1,3-dioxane, methyl and propyl para-hydroxybenzoates, and mixtures of such benzoates with sodium dehydroacetate, sorbic acid, and imidazolidinyl urea.

The compositions of the Present invention may also be formulated to include dyes, colorants, reducing agents, neutralizing agents, and preservatives, necessary for their application as permanent wave systems or hair dyes, for example. The active formulation can be applied in several different forms including lotions, gels, mousses, aerosols, and pump sprays, for example, and as conditioners and shampoos. The active ingredient includes a solvent, and suitable solvent fluids for hair care formulations are water as well as, for example, such fluids as alcohols namely ethanol or isopropanol, hydrocarbons and halogenated hydrocarbons such as mineral spirits and trichloroethane, supercritical fluids such as supercritical carbon dioxide and nitrogen, cyclic siloxanes, and aerosol propellants. In those instances where it is desired to incorporate the active in the form of either an emulsion or microemulsion, such emulsions may be prepared in accordance with either U.S. Pat. No. 4,501,619, issued Feb. 26, 1985, which is directed to emulsions, or U.S. Pat. No. 4,620,878, issued Nov. 4, 1986, relating to microemulsions, each of which is incorporated herein by reference.

When the composition is intended for aerosol application, propellant gases can be included such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether. Where the solvent system is alcohol free, mechanical and chemical drying agents may also be employed in spray and aerosol formulations.

It will be apparent from the foregoing that many other variations and modifications may be made in the compounds, compositions, and methods, described herein, without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. In a hairstyling preparation which includes as ingredients thereof an anionic organic polymeric film forming resin which is a polyacrylate and an alcohol solvent, the improvement comprising incorporating into the hairstyling preparation as an ingredient thereof an amidofunctional polysiloxane having an average of fifty to one thousand siloxane units per molecule with an average of one to fifty of the siloxane units per molecule being amide-containing siloxane units bearing a substituent of the formula:

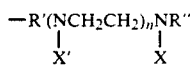

wherein n has a value of zero or one; R' is an alkylene radical of three to six carbon atoms; R" is a hydrogen radical or an alkyl radical of one to six carbon atoms; X is an acyl radical of the formula:

X' is a hydrogen radical or X; R''' is an alkyl radical of one to four carbon atoms; and wherein substantially all other organic substituents in the polysiloxane are methyl groups said organic polymeric film forming resin and said amidofunctional polysiloxane being present in the hairstyling preparation in a weight ratio from 2:1 to 1:2.

2. The preparation of claim 1 in which the anionic polyacrylate film forming resin is poly(methylvinyl) ether/maleic acid) monoethyl ester.

3. The preparation of claim 1 in which the amidofunctional polysiloxane and the organic film forming resin are present in the preparation in a weight ratio of bout 1:1.

4. In a method of styling hair wherein a hairstyling preparation is applied to the hair which includes as ingredients thereof an anionic organic polymeric film forming resin which is a polyacrylate and an alcohol solvent, the improvement comprising incorporating into the hairstyling preparation as an ingredient thereof prior to application of the hairstyling preparation to the hair, an amidofunctional polysiloxane having an average of fifty to one thousand siloxane units per molecule with an average of one to fifty of the siloxane units per molecule being amide-containing siloxane units bearing a substituent of the formula:

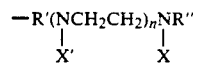

wherein n has a value of zero or one; R' is an alkylene radical of three to six carbon atoms; R'''is a hydrogen radical or an alkyl radical of one to six carbon atoms; X is an acyl radical of the formula:

X' is a hydrogen radical or X; R''' is an alkyl radical of one to four carbon atoms; and wherein substantially all other organic substituents in the polysiloxane are methyl groups said organic polymeric film forming resin and said amidofunctional polysiloxane being present in the hairstyling preparation in a weight ratio from 2:1 to 1:2.

5. The method of claim 4 in which the anionic polyacrylate film forming resin is poly(methylvinyl ether/-maleic acid) monoethyl ester.

6. The method of claim 4 in which the amidofunctional polysiloxane and the organic film forming resin are present in the preparation in a weight ratio of about 1:1.

* * * * *